(12) United States Patent
Tewolde et al.

(10) Patent No.: US 11,971,311 B2
(45) Date of Patent: Apr. 30, 2024

(54) INFRARED BASED CORE BODY TEMPERATURE SENSING SYSTEM AND METHOD

(71) Applicant: XTemp LLC, Dallas, TX (US)

(72) Inventors: Senay Tewolde, Dallas, TX (US); Katharine Renee Long, Lubbock, TX (US)

(73) Assignee: XTemp LLC, Dallas, TX (US)

( * ) Notice: Subject to any disclaimer, the term of this patent is extended or adjusted under 35 U.S.C. 154(b) by 747 days.

(21) Appl. No.: 17/100,482

(22) Filed: Nov. 20, 2020

(65) Prior Publication Data

US 2021/0156749 A1 May 27, 2021

Related U.S. Application Data

(60) Provisional application No. 62/939,443, filed on Nov. 22, 2019.

(51) Int. Cl.
*G01K 13/20* (2021.01)
*A61B 5/01* (2006.01)
*G06T 5/50* (2006.01)

(52) U.S. Cl.
CPC .............. *G01K 13/223* (2021.01); *A61B 5/01* (2013.01); *G06T 5/50* (2013.01); *G06T 2207/10048* (2013.01); *G06T 2207/30041* (2013.01)

(58) Field of Classification Search
CPC .......... G01K 13/223; A61B 5/01; G06T 5/50; G06T 2207/10048; G06T 2207/30041
See application file for complete search history.

(56) References Cited

PUBLICATIONS

Tewolde, A model for noninvasive diagnosis of eye tumor and estimation of core body temperature by ocular surface temperature, 2015, Texas Tech University Libraries, Dissertations, pages i-ix and 1-112 (Year: 2015).*
Tan et al, Infrared thermography on ocular surface temperature: A review, 2009, Elsevier, Infrared Physics and Technology 52(2009), pp. 97-108 (Year: 2009).*

* cited by examiner

*Primary Examiner* — Rochelle D Turchen
(74) *Attorney, Agent, or Firm* — Scale LLP

(57) ABSTRACT

A non-invasive and a non-contact core body temperature monitoring method and system including an infrared camera, a processor, and a non-transitory computer readable medium with a program for analyzing thermal images of the human eye. The method for using the system that includes isolating ocular thermal images from a facial image; extracting thermal information about the surface of the eye; transitioning the thermal information to a selected model of the eye; estimating a temperature at the back of the eye; optimizing the estimated temperature at the back of the eye, and transmitting the optimized temperature information to an output device.

20 Claims, 7 Drawing Sheets

INFRARED BASED CORE BODY TEMPERATURE SENSING SYSTEM AND METHOD

FIELD OF THE INVENTION

The present invention generally relates to measurement of body temperature, specifically, core body temperature based on measured temperature on the ocular surface together with a heat transfer model to recover the core temperature behind the eye.

BACKGROUND OF THE INVENTION

Body temperature is one of the most important and oldest indices of human physiological condition. While body temperature varies from person to person and from time to time, the human body manages to maintain a relatively constant core temperature in a range of about 36.8 to 37.7° C. through the physiological process called thermoregulation.

Surface body temperatures are known to deviate from core body temperature with a high degree of variation based on individual body characteristics and the location on the body where the temperature is measured. Core body temperature is recognized as a more accurate indicator of physiological condition of the body than surface body temperature measurements.

Accurate monitoring of core body temperature typically requires invasive measurement at different sites, i.e. inserting catheters equipped with thermometers pulmonary artery, esophagus, bladder, rectum, nasopharynx, and temporal artery. However, these measurements are limited by the inconvenient operational settings of the probes. For example, a pulmonary artery catheter is considered by many health practitioners to be the most accurate measurement of core body temperature. A temperature sensor mounted on the pulmonary artery catheter is inserted into the pulmonary artery and measures the temperature of the blood flowing from the heart to the lung. However, this procedure is very invasive and is associated with some risks and complications.

Other invasive methods such as rectal probes and urinary catheter have measurement disparity compared with other measurement methods. For instance, rectal temperature is often higher than the temperature measured at different site, and it is also known for its slow response to temperature changes. The bladder (urinary) temperature measurement is considered accurate but has a tendency to be influenced by the amount of the urine flow. Other additional concerns include the risk of perforation of the tissue during insertion of the probe/catheter and inaccurate measurement due to the displacement or detachment of the temperature sensors.

Noninvasive temperature measurement is another method used in monitoring core body temperature. The most widely used methods are the infrared radiation ear device (IRED), infrared thermography, and oral probes. These methods, however, are known for their lack of accuracy and consistency. For instance, differences are observed between left and right ears, IRED has poor measurement repeatability, and its measurement accuracy can be greatly impacted by operator technique, patient anatomy (measurement site), positioning of the probe in the ear canal, and the sensitivity of the probe to detect radiation emitted from both the tympanic membrane and the aural canal.

Another type of infrared thermometer commonly used for core body temperature measurement is the forehead scanning probe. The accuracy of the probe has shown a favorable outcome in children; however, the probe accuracy has shown to be affected by the environmental conditions and physical factors such as sweating, exposing to freezing or warm environment, or fluctuating body mass.

Temperature screening of the inner canthus of the eye is considered as the most suitable location for remotely monitoring core body temperature. As a result, the measurement site has been used in mass screening during infectious disease outbreaks, such as SARS (Severe Acute Respiratory Syndrome), avian influenza, Ebola, COVID-19 etc. Even though the inner canthus of the eye is the most consistently warmest part of the facial surface, the measurement has proven to be inconsistent and the number of thermal pixels captured from the inner canthus may not be adequate enough to indicate the small temperature difference between a healthy individual and someone with a fever.

Another noninvasive technique is a zero-heat-flux thermometry, which is used for deep tissue temperature monitoring. Even though it is easy to operate and provides continuous measurements, the accuracy of the measurement depends on a tight adhesion of a temperature probe to the skin, skin perfusion, and physiological changes. Small air gaps between the temperature probe and the skin surface are known to reduce the accuracy of the temperature measurement.

A shortcoming of existing core body temperature methods is the need for physical contact with the body, which may increase the chance of transmission of a disease between patient and clinician.

Even without physical contact, a shortcoming of measuring core body temperature based on the surface skin temperature (forehead, temporal lobe, arms) or tear duct regions is that the temperatures of these regions are easily affected by environmental conditions, physical exercise, and physiological conditions.

Another shortcoming of existing core body temperature methods when used in the context of estimating time of death is that they use muscle and rectal tissues where temperature plateau phenomena increase error in determining the time of death.

Another shortcoming of existing core body temperature methods is slow response to temperature changes in the body or requiring preplanning in implementation of the temperature measurement technique.

Another shortcoming of existing core body temperature methods is the level of invasiveness and inconvenience for the invasive methods, and measurement accuracy and repeatability for the noninvasive methods.

Therefore, an unmet need exists for a core body temperature method and system that does not require physical contact with the patient, provides reliable postmortem time information, and can monitor rapid changes in core body temperature without preplanning.

SUMMARY OF THE DISCLOSURE

The present invention is a system and method for measuring core body temperature. Specifically, estimating a core body temperature at the back of the eye based on a measurement of the ocular surface using an infrared thermal camera directed to the eye.

One embodiment of the present disclosure is an infrared temperature estimating method including the steps of: localization of the ocular surface in the thermal image; transitioning temperature data from a thermal image of an ocular surface of an eye to an ocular surface of a finite element mesh of the eye model; and estimating a core body temperature at the back of the eye model. The method may further include the step of: transmitting the estimated core body temperature to an output device. The method may further include the steps of: mapping method between optical and thermal images; obtaining the thermal image of the ocular surface of the eye; and extracting the temperature data from the thermal image of the ocular surface using knowledge of the camera's response. The method may further include the steps of: detecting at least part of a facial surface comprising the ocular surface of the eye; acquiring a facial thermal image of the at least part of the facial surface; and transmitting the facial thermal image to the processor, where the facial thermal image comprises the thermal image of the ocular surface of the eye. The estimating step may include using models of heat transfer to map between core temperature and temperatures on the ocular surface; and performing a gradient-based or non-gradient-based optimization procedure to estimate the core body temperature at the back of the eye that produces the ocular surface temperature profile that best fits the data according to some merit function. The transition step may include applying temperature data from pixel positions of the thermal image of the ocular surface of the eye to 3D Cartesian coordinates on the ocular surface of a mesh or other discretized model of the eye's geometry. The method may further include the step of: constructing the model of the eye based on thermophysical properties and boundaries of a cornea, an anterior humor, a vitreous humor, a lens, a retina, a choroid, an iris, a ciliary body, and a sclera of an eye. In some embodiments, the core temperature may be estimated using the weak equation:

$$\int_R (k_{eff} + k_i) \nabla w \cdot \nabla T dR +$$
$$\int_{\Gamma_u = \Gamma_2 \cup \Gamma_3} w[h_\infty(T - T_\infty) + \sigma\varepsilon(T^4 - T_\infty^4) + E_v] d\Gamma_u +$$
$$\int_{\Gamma_1} wh_b(T - T_{d\_core}) d\Gamma_1 - \int_R wQ_{eff} dR = 0 \; \forall \; w \in H^1 \; i = 2\ldots5$$

where $H^1$ is the Sobolev space of weakly once-differentiable functions, $k_{eff}$ is the effective value of the thermal conductivity of eye tissue, $k_i$ is the thermal conductivity of eye tissue in region i, w is the test function such that $w \in C^n(R)$ ($C^n$ is a continuous function of n derivatives and R is the eye domain such that $R \cup \mathbb{R}^d$) $\Gamma_1$ is part of the eye surface that is not exposed to the surrounding air, and $\Gamma_2 \cup \Gamma_3$ is part of the eye surface that is exposed to the surrounding air, T is the ocular surface temperature at $\Gamma_2 \cup \Gamma_3$ and the estimated core body temperature (the surface temperature at the back of the eye) at $\Gamma_1$, $T_\infty$ is ambient temperature, $\varepsilon$ is emissivity, $\sigma$ is the Boltzmann constant, $E_v$ is tear evaporative heat flux, $Q_{eff}$ is the effective volumetric heat generation rate due to metabolism, $T_{d\_core}$ is the default core body temperature (typically set by the user), $h_\infty$ is convective heat transfer coefficient between the tear film and the surrounding air, and $h_b$ is the convective heat transfer coefficient between the vascular region ($R_1$) and the surrounding blood.

Another embodiment of the present disclosure may include a system for estimating a core body temperature, including: a non-transitory computer-readable medium in communication with a processor and comprising a program that, when executed, performs a method, the method including: transitioning temperature data from a thermal image of an ocular surface of an eye to the ocular surface of a model of the eye; and estimating the core body temperature at the back of the eye model. The system may include an infrared camera in communication with the processor. The system may include an output device in communication with the processor.

Examples of the more important features of the disclosure have been summarized rather broadly in order that the detailed description thereof that follows may be better understood and in order that the contributions they represent to the art may be appreciated. There are, of course, additional features of the disclosure that will be described hereinafter and which will form the subject of the claims appended hereto.

BRIEF DESCRIPTION OF THE DRAWINGS

The organization and manner of the structure and operation of the invention, together with further objects and advantages thereof, may best be understood by reference to the following description taken in connection with the accompanying drawings wherein like reference numerals identify like elements in which.

DETAILED DESCRIPTION OF THE DISCLOSURE

Figure 1:
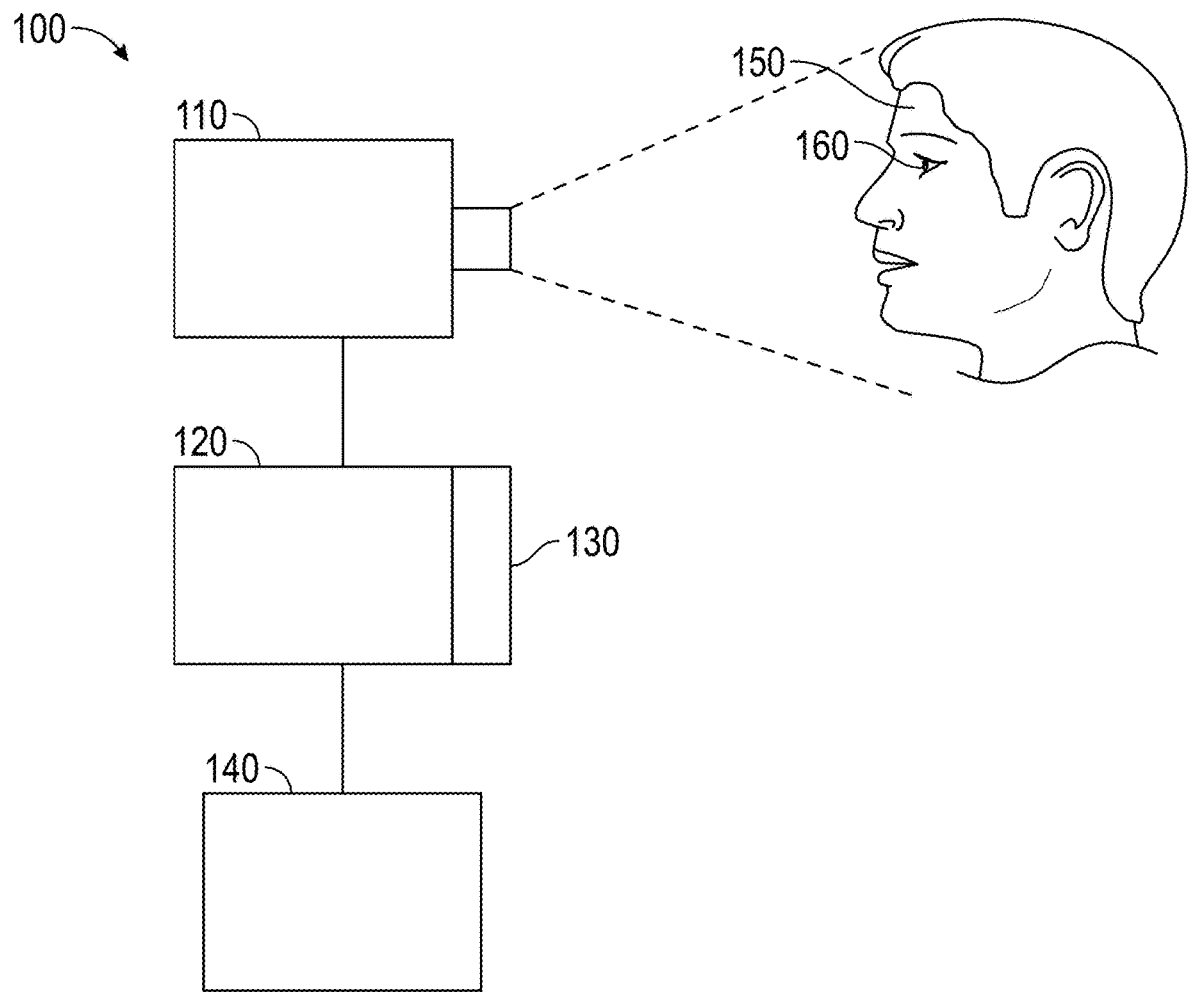
FIG. 1 is a diagram of a system for estimating core body temperature using a thermal image according to one embodiment of the present disclosure.

While this invention may be susceptible to embodiment in different forms, specific embodiments are shown in the drawings and will be described herein in detail with the understanding that the present disclosure is to be considered an exemplification of the principles of the invention and is not intended to limit the invention to that as illustrated.

Figure 2:
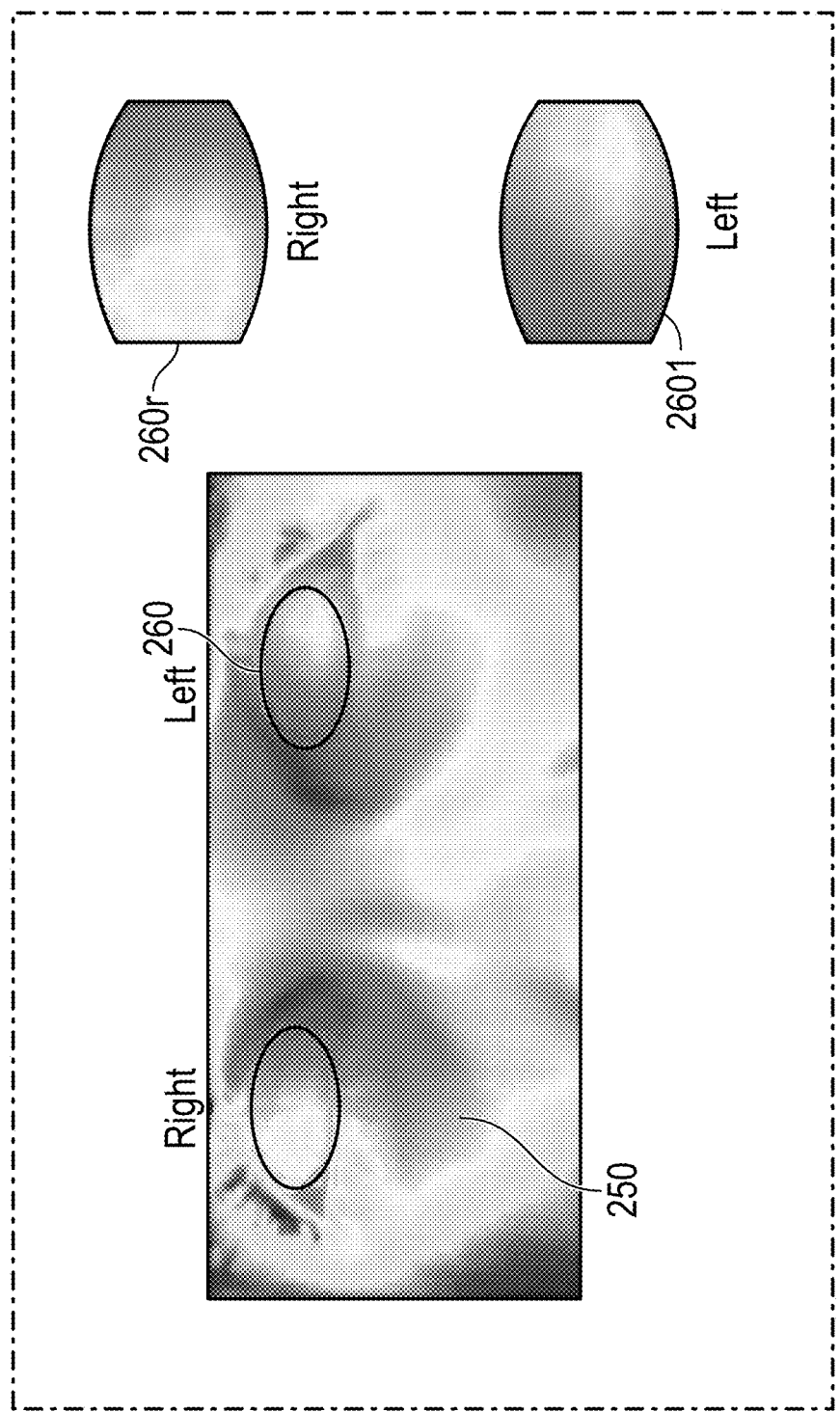
FIG. 2 is a thermal image prepared using the system of FIG. 1.

FIG. 1 shows a system 100 for monitoring the core body temperature of a human body remotely. The system includes optical (visible light) and infrared cameras 110 that can be used to acquire optical and thermal images of an ocular surface 160 of a human, respectively. The thermal image of the ocular surface may be a part of a thermal image of a facial surface 150 or of a thermal image of one or both eyes. In some embodiments, the optical image of one or both eyes may be derived from the image of the facial surface 150. The system 100 includes a processor 120 in communication with the optical and infrared cameras 110 and configured to receive the thermal image data. The processor 120 may be in communication with a memory 130 storing a program that, when executed, may perform a method to process the thermal image data. The memory 130 may be a non-transitory, computer readable medium, as would be understood by a person of ordinary skill in the art. The system 100 may also include an output device 140, such as a monitor, a transmitter, a memory, or a printer, for receiving information containing the core body temperature estimated by the processor 120 through the execution of the program on the memory 130. FIG. 2 shows a facial thermal image 250, corresponding to the facial surface 150, and ocular surface thermal images 260, corresponding to the ocular surfaces 160.

Figure 3:
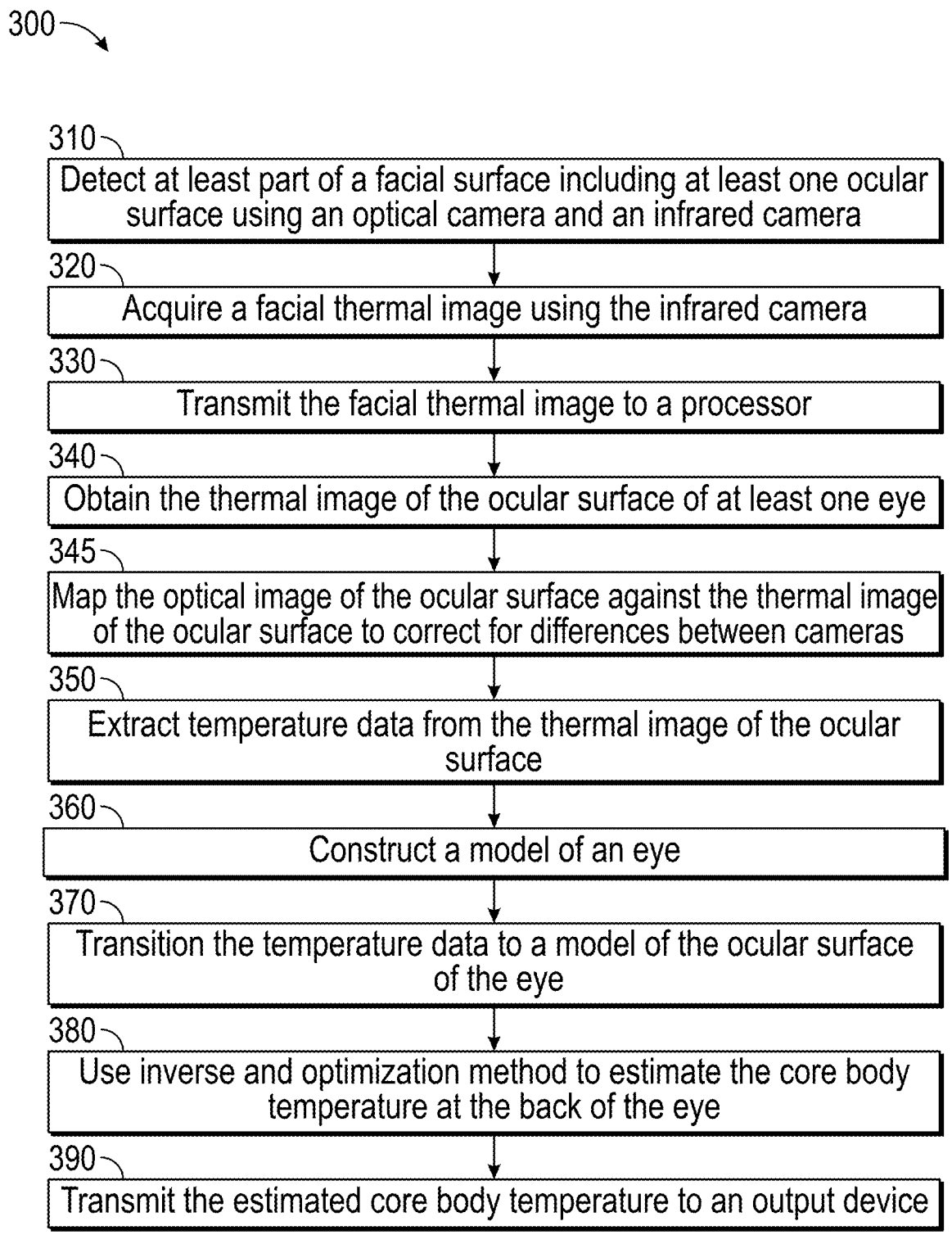
FIG. 3 shows a flow chart of a method of estimating core body temperature according to one embodiment of the present disclosure.

FIG. 3 shows a method 300 of estimating a core body temperature according to one embodiment of the present disclosure. In step 310, at least part of the facial surface 150 including at least one ocular surface 160 may be detected by the optical and infrared cameras 110. In step 320, the facial thermal image 250 may be acquired by the infrared camera 110.

In step 330, the facial thermal image 250 may be transmitted from the infrared camera 110 to the processor 120. In step 340, the processor 120, executing the program on the memory of a local machine or cloud computer 130, may extract the thermal image of the right eye 260r and/or the left eye 260l. Step 340 may be performed automatically or may be manually performed by a person controlling the isolation of the ocular surface thermal images 260 of one or both eyes. In some embodiments, step 340 may include facial feature detection where facial landmarks are identified to localize and isolate the eye regions 260 from the facial thermal image 250. The processor 120 may first identify the location of a face from the image 250 transferred from the infrared camera 110 using one or more of: Haar cascades, pre-trained Histogram of Oriented Gradients and Linear and support vector machine object detector, and deep learning-based algorithms. Once the location of the face is confirmed, then the processor 120 may execute a program for facial landmark detection to first identify eye regions, and, then, isolate the ocular surface thermal image 260 from the facial thermal image 250. The facial landmark detection may be based on pre-trained facial landmark images where ensemble regression trees are trained to estimate the facial landmark positions directly from pixel intensities. The facial landmark detection may be performed using a location of 68 (x, y) coordinate points iBUG 300-W dataset. The use of the iBug-W dataset is exemplary and illustrative only, as other suitable datasets known to persons of skill in the art may also be used, such as a 194 coordinate points HELEN dataset. The facial landmark detector may also be equipped with eye blink detection feature, where it can distinguish open eyes from closed once. The purpose of the blink feature is to track the eyes and facilitate automatic capture of the ocular surface images from open eyes from a recorded or live streaming infrared thermal image.

In step 345, one of the optical image and the thermal image is mapped onto the other in order to correct for differences (image sizes, mounting orientations, fields of view, etc.) due to multiple cameras 110 being used to capture the optical and thermal images. This step is optional and may not be necessary when using a single camera that can capture both optical and infrared images. Once step 345 is complete, future performance of the method 300 may use the mapping information from previous performances, thus, step 345, if needed, is only performed once per set up of the cameras 110. Ocular landmark points (pixel locations) in the optical images may be used as a reference points to locate the ocular landmark points in the thermal images. This mapping process may use homography or geometric-based mapping.

Homography mapping is performed by selecting 4-8 points in the optical image and the corresponding thermal image to set up an initial pixel correspondence between the two cameras 110. Then a homograph may be constructed based on those data points that can then be used to map pixel locations in the optical image onto the thermal image. Geometric-based mapping is performed by using the inner canthi locations in both the optical and thermal images as anchor points (or fixed points of reference). In the thermal image, the inner canthi are most consistently warmest part of the facial surface; hence, different methods can be used to locate the inner canthi, such as 1) a localized search of the pixels around the eye region with the warmest temperature values and 2) use of machine learning to identify location of the inner canthi. In the optical image, the location of the inner canthi may be obtained from the ocular landmark points. Following the localization of the inner canthi, the geometry of both images and the relationship between the image dimensions and Field of Views of the chosen cameras may then be used to map the ocular landmark points from the optical image onto the thermal image. Both homography and geometric based mapping require that the cameras 110 be in close proximity to each other during the taking of the optical and thermal images, usually between 0.5 and 2.5 inches, in order to reduce the effect of parallax.

In step 350, temperature data may be extracted from the ocular surface thermal images 260 of the one or both eyes. Temperature data extraction may include filtering temperature values within segmented regions of the ocular surface 160.

In step 360, a model 400 of the eye may be constructed with the considerations of different regions: cornea, anterior and vitreous humor, lens, retina, choroid, iris, ciliary body, and sclera, grouped based on their thermophysical properties. In some embodiments, step 360 may be optional, especially if the eye model 400 has been previously constructed or provided. The eye model 400 selected to be used to establish boundary conditions may differ based on the patient. Different sizes of eye models, ranging from an infant to an adult size, may be constructed using CAD and meshing software. The goal is to approximately match the eyeball sizes of different age groups for an accurate estimate of core body temperature. The globes of the eye models are assumed to be axisymmetric with respect to the optical axis. The anterior and posterior regions of the eye 500 are composed of vascular and avascular tissue structures (See FIG. 5), where the avascular part of the eye is composed of cornea 520, anterior chamber (aqueous humor) 530, lens 540, and vitreous humor 550, and the vascular structure 510 is composed of retina & choroid 514, iris & ciliary body 516, and sclera 512. Due to similarities in thermophysical properties, an eye model may be constructed by summarizing or using representative structures of the eye for arrive at an eye model using five regions—$R_1$-$R_5$ in Table 1. The thermophysical properties and other parameters of the eye model 400 are obtained from a wide range of literature and are expressed as statistical values (i.e., mean±SD).

TABLE 1

Figure 5:
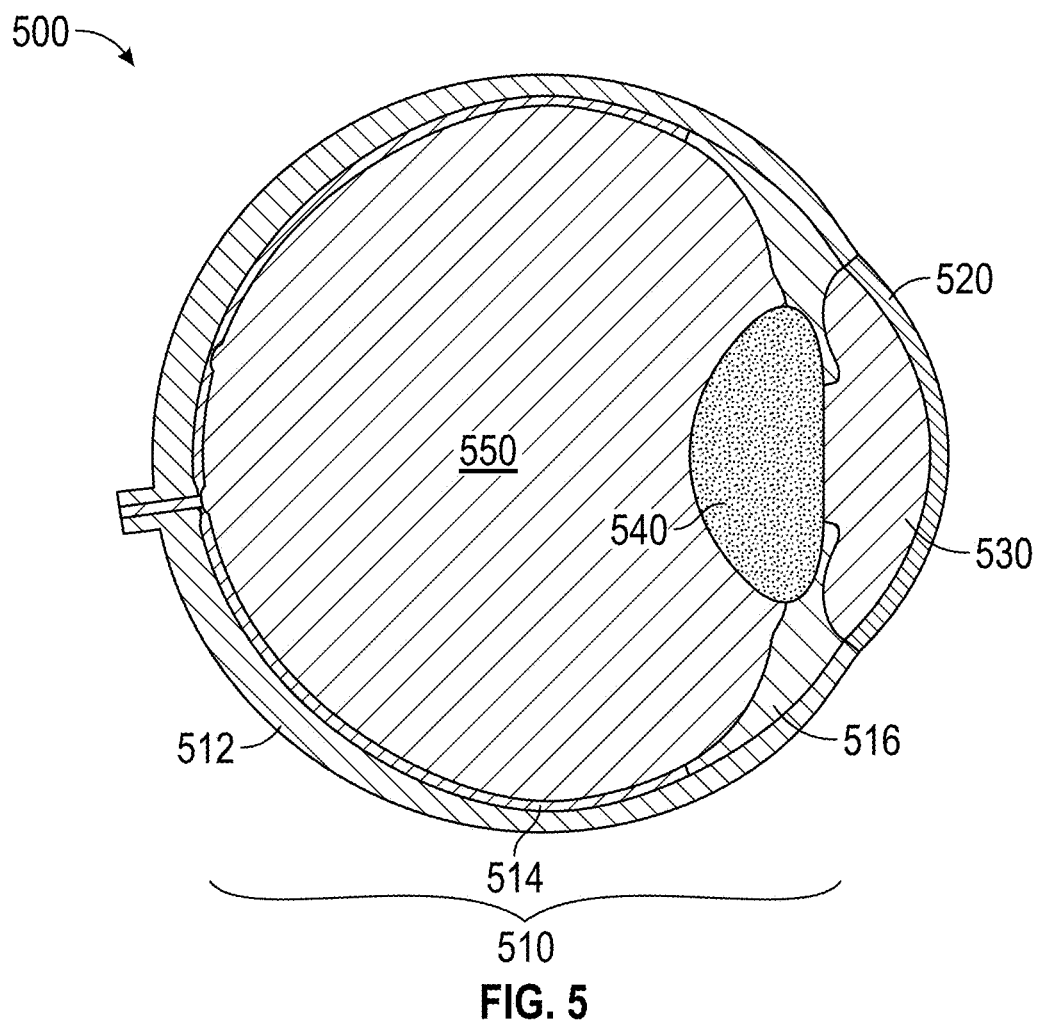
FIG. 5 is a diagram of an adult human eye model depicting the different regions considered in the formulating the mathematical model.

Thermophysical properties of eye tissues (see FIG. 5)

| Eye Regions | Tissue | Thermal conductivity, k [W/m-K] | Specific heat, $C_p$ [J/kg-K] | Density, ρ [kg/m³] |
|---|---|---|---|---|
| $R_1$ | Sclera/Retina/Iris/Choroid | 1.0042 ± 0.04 | 4200 | 1032 |
| $R_2$ | Cornea | 0.58 ± 0.06 | 3515 | 1052 |
| $R_3$ | Aqueous | 0.58 ± 0.01 | 3997 | 1003 |
| $R_4$ | Lens | 0.43 ± 0.05 | 3133 | 1076 |
| $R_5$ | Vitreous | 0.59 ± 0.01 | 4047 | 1005 |
|  | Blood | 0.53 ± 0.04 | 3617 | 1050 |

Temperature distribution within the eye may be formulated using an energy equation where the vascular region of the eye includes two energy equations, while the avascular region is treated as a solid tissue. In the vascular region 510 of the eye ($R_1$), for blood:

$$\nabla(\varphi k_b \nabla T_b) + h_{tb} a_{tb}(T_s - T_b) = \varphi \rho_b c_{p_b}\left(\frac{\partial T_b}{\partial t} + \vec{v}_b \cdot \nabla T_b\right), \text{ in } R_1 \quad (1)$$

For tissue:

$$\nabla \cdot ((1-\varphi)k_s \nabla T_s) + (1-\varphi)Q_m + h_{tb}a_{tb}(T_b - T_s) = (1-\varphi)\rho_s c_{p_s}\frac{\partial T_s}{\partial t}, \quad (2)$$

$$\text{in } R_1$$

In the avascular region 520, 530, 540, 550 of the eye ($R_i$):

$$\nabla \cdot (k_i \nabla T_i) = \rho_i c_{p_i}\frac{\partial T_i}{\partial t}, \text{ in } R_i, i=2\ldots 5 \quad (3)$$

where $R_1$ and $R_i$ (i=2 ... 5) represent the vascular and avascular regions (Table 1) in the eyeball, respectively; $k_i$, $k_s$ and $k_b$ are the thermal conductivities of the avascular tissue (in $R_i$, i=2 ... 5), vascular tissue (in $R_1$) and blood, respectively; φ is the porosity of $R_1$; $T_b$ and $T_s$ are the temperature of the blood and tissue in $R_1$, respectively; $T_i$ is the temperature of the avascular tissue in $R_i$ (i=2 ... 5); $h_{tb}$ is the convective heat transfer coefficient between blood and tissue structure; $a_{tb}$ is the specific surface area; $Q_m$ is the volumetric heat generation rates due to metabolism; $\rho_s$, $c_{p_s}$ and $\sigma_b$, $c_{p_b}$ are the densities and specific heats of the tissue and blood in $R_1$, respectively; $\rho_i$ and $c_{p_i}$ are the densities and specific heats of the avascular tissue in $R_i$ (i=2 ... 5), respectively; and $\vec{v}_b$ is the blood flow velocity.

The governing equations are simplified by assuming steady state. For the vascular region, the two energy equations are coupled by the convective heat transfer term, $h_{tb} a_{tb} (T_b-T_s)$:

$$\nabla \cdot (\varphi k_b \nabla T_b) + \nabla \cdot ((1-\varphi)k_s \nabla T_s) - \varphi \rho_b c_{p_b} \vec{v}_b \cdot \nabla T_b + (1-\varphi)Q_m = 0, \text{ in } R_1 \quad (4)$$

The above equation may be further simplified by assuming the capillary vessels within the vascular tissue are thermally insignificant; meaning, there is no temperature difference between tissue and blood, i.e. $T_s = T_b$, leading to:

$$\vec{v}_b \cdot \nabla T_b \approx \omega_b (T_s - T_b) = 0 \text{ in } R_1 \quad (5)$$

where $\omega_b$ is the perfusion rate of blood, defined as volume flow rate of blood per unit volume of the vascular tissue, in mL-blood/[(mL-tissue)-sec]. The temperatures $T_s$ and $T_b$ collectively are represented as $T_1$ ($T_s = T_b = T_1$). The vascular equation can then be represented as:

$$\nabla \cdot ((\varphi k_b \nabla T_1) + \nabla \cdot ((1-\varphi)k_s \nabla T_1) - (1-\varphi)Q_m = 0, \text{ in } R_1 \quad (6)$$

$$\nabla \cdot (\nabla T_1(\varphi k_b + (1-\varphi)k_s)) - (1-\varphi)Q_m = 0, \text{ in } R_1 \quad (7)$$

$$k_{eff} = \varphi k_b + (1-\varphi)k_s \text{ and } Q_{eff} = (1-\varphi)Q_m \quad (8)$$

$$\nabla \cdot (k_{eff} \nabla T_1) - Q_{eff} = 0, \text{ in } R_1 \quad (9)$$

where $k_{eff}$ is the effective value of the thermal conductivity of eye tissue and $Q_{eff}$ is the effective volumetric heat generation rate due to metabolism The avascular region 520, 530, 540, 550 may be expressed as:

$$\nabla \cdot (k_i \nabla T_i) = 0, \text{ in } R_i, i=2\ldots 5 \quad (10)$$

Table 2 shows the design parameters considered in the eye model. Although some of the parameters, such as convective heat transfer coefficient of the blood, porosity, and emissivity, are assumed to be constant, the ambient temperature, convective heat transfer coefficient of the air are expected to vary with the environmental conditions. The parameter values shown in Table 2 are designed to represent eye model in a controlled indoor environment.

TABLE 2

Values of parameters used in eye model

| Parameter | Description/Unit | Value |
|---|---|---|
| $h_\infty$ | Convective heat transfer coefficient between the tear film and the surrounding air [W/m²-K]* | 10 ± 2.5 |
| $h_b$ | Convective heat transfer coefficient between the vascular region ($R_1$) and the surrounding blood [W/m²-K] | 110 ± 10 |
| σ | Stefan Boltzmann constant [W/m²-K4] | $5.67 \times 10^{-8}$ |
| ε | Emissivity | 0.975 ± 0.021 |
| $E_v$ | Tear evaporative heat flux [W/m²]* | 40 ± 2.0 |
| $T_\infty$ | Ambient temperature [° C.]* | 23 ± 1.0 |
| φ | Porosity of the healthy vascular tissue | 0.3 ± 0.03 |
| $Q_m$ | Metabolic heat generation [W/m³] |  |

*Subject to change based on the environmental condition

Combination the vascular and avascular equations will provide the mathematical formulation necessary for solving the core body temperature as the boundary condition of the sclera surface that is not exposed to the surrounding air.

$$\nabla \cdot (k_{eff} \nabla T_1) \cdot \nabla \cdot (k_i \nabla T_i) - Q_{eff} = 0, \text{ in } R_i, i=2\ldots 5 \quad (11)$$

Figure 6A:
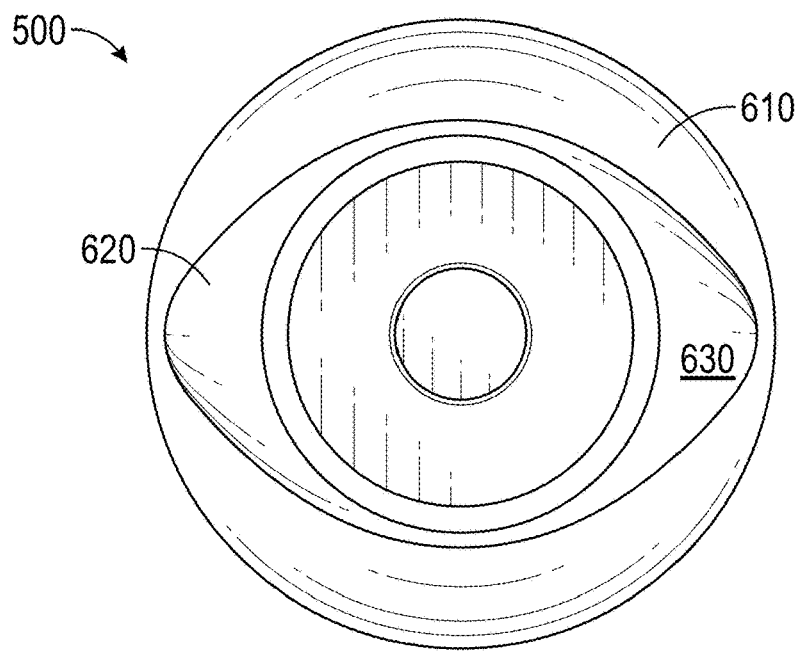
FIG. 6A is a diagram of the boundary layers of the eye model as seen from the front according to one embodiment of the present disclosure.
Figure 6B:
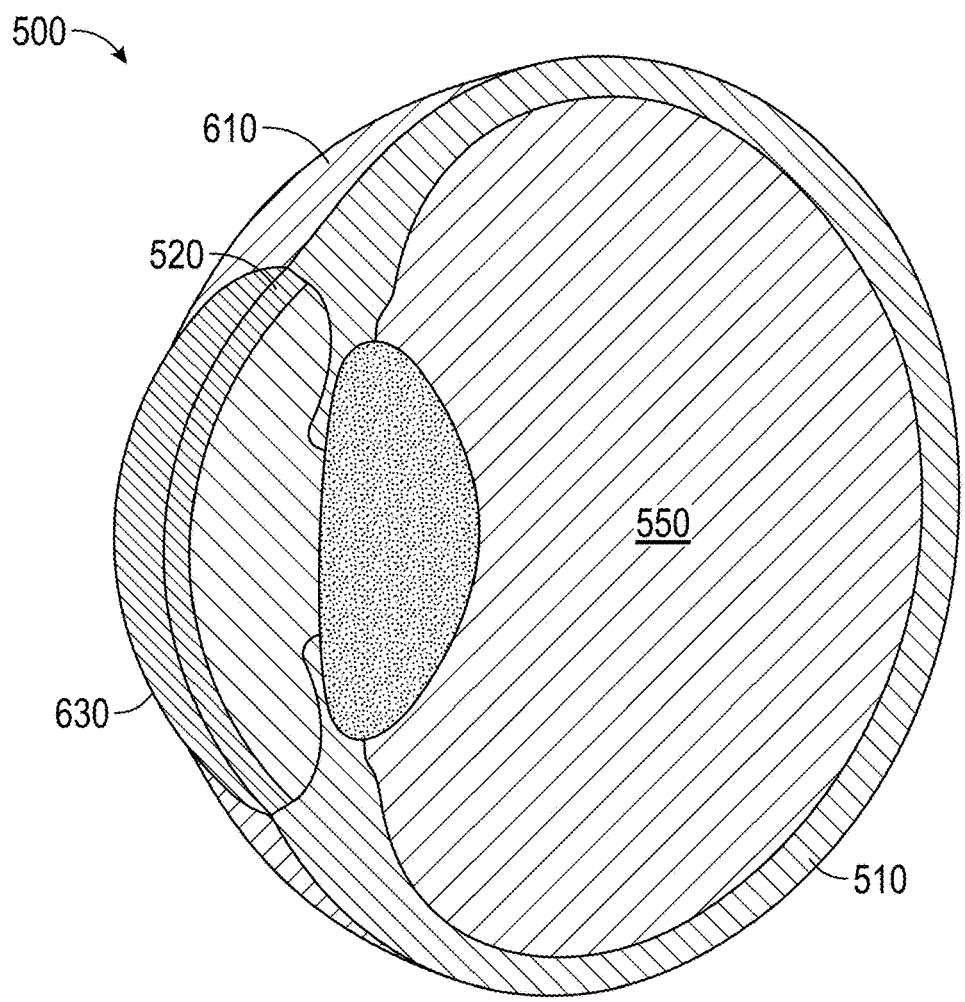
FIG. 6B is a diagram of the boundary layers of the eye model of FIG. 6A as a side cross-section.

The boundary condition for the vascular surface of the sclera not exposed to the surrounding air 610 (See FIGS. 6A-6B), $\Gamma_1$ is:

$$-k_{eff}\frac{\partial T_1}{\partial n_1} = h_b(T_1 - T_{d\_core}), \text{ on } \Gamma_1 \quad (12)$$

where $h_b$ is the convective heat transfer coefficient between the vascular region 510 ($R_1$) and the surrounding blood, and $$\frac{\partial T_1}{\partial n_1}$$

is the vascular temperature gradient in the direction of outward unit vector ($n_1$) normal to $\Gamma_1$ of $R_1$. $T_{d\_core}$ is the default core body temperature and $T_1$ is the vascular tissue temperature distribution of $R_1$.

The boundary condition for the vascular surface of the sclera exposed to the surrounding air 620, $\Gamma_2$ is:

$$-k_{\mathit{eff}} \frac{\partial T_1}{\partial n_1} = h_\infty(T_1 - T_\infty) + \sigma\varepsilon\left(T_1^4 - T_\infty^4\right) + E_v, \text{ on } \Gamma_2 \quad (13)$$

The vascular surface 620 is subjected to both radiative and convective heat transfer, as well as evaporation from the tear film to the surrounding air.

$$\frac{\partial T_1}{\partial n_1}$$

is the vascular temperature gradient in the direction of outward unit vector ($n_1$) normal to $\Gamma_2$ of $R_1$, $h_\infty$ is the convective heat transfer coefficient between the tear film and the surrounding air, $\sigma$ is the Stefan-Boltzmann constant, $\varepsilon$ is the ocular surface emissivity, $T_\infty$ is the ambient air temperature, $E_v$ is the tear evaporative heat flux. Values of the parameters used in the above equations, including the thermophysical properties, are summarized in Tables 1 and 2.

The interfacial conditions between two contiguous regions are described by the continuity condition:

$$\left. \begin{array}{l} k_{\mathit{eff}} \dfrac{\partial T_1}{\partial n_1} = -k_i \dfrac{\partial T_i}{\partial n_i} \\ T_1 = T_i \end{array} \right\}, \text{ on } IR_{1i} \ i = 2 \ldots 5 \quad (14)$$

where $IR_{1i}$ is the interface between the vascular region $R_1$ and the neighboring avascular regions $R_i$ (i=2 ... 5); $k_i$ and $T_i$ are the thermal conductivity and the temperature distribution of $R_i$ (i=2 ... 5), respectively.

The boundary condition avascular surface 630 of the cornea $\Gamma_3$ (FIGS. 6A-6B) is:

$$-k_3 \frac{\partial T_3}{\partial n_3} = h_\infty(T_3 - T_\infty) + \sigma\varepsilon\left(T_3^4 - T_\infty^4\right) + E_v, \text{ on } \Gamma_3 \quad (15)$$

where $k_3$ and $T_3$ are the thermal conductivity and temperature of the cornea tissue of the avascular region $R_2$, respectively, $$\frac{\partial T_3}{\partial n_3}$$

is the avascular temperature gradient in the direction of outward unit vector ($n_3$) normal to $\Gamma_3$ of $R_2$.

$$\int_R (k_{\mathit{eff}} + k_i)\nabla w \cdot \nabla T dR + \quad (19)$$
$$\int_{\Gamma_u = \Gamma_2 \cup \Gamma_3} w\left[h_\infty(T - T_\infty) + \varepsilon\left(T^4 - T_\infty^4\right) + E_v\right]d\Gamma_u +$$
$$\int_{\Gamma_1} wh_b(T - T_{d\_core})d\Gamma_1 - \int_R wQ_{\mathit{eff}} dR = 0 \ \forall \ w \in H^1 \ i = 2 \ldots 5$$

where the eye domain $R \cup \mathbb{R}^d$ the unknown temperature of the tissue $T \in C^n$ (R) (where $C^n$ is a continuous function of n derivatives), and a test function w such that $w \in C^n(R)$. Equation 19 is the final mathematical model that estimates the core body temperature.

In some embodiments, an approximate solution to this mathematical model is computed numerically using techniques that may include fixed-point iteration, Newton's method, or a quasi-Newton method for handling the non-linear radiative term, and techniques that may include direct solvers or preconditioned iterative solvers for systems of linear equations.

In step 370, the temperature data may be transitioned from their pixel position in the ocular surface thermal image 260 to corresponding Cartesian coordinates 410 (see FIG. 4A) of a finite element mesh 400 of the eye model or another discretized model of the eye's geometry. The use of a Cartesian coordinate set is exemplary and illustrative only, as other coordinate systems may be used as would be understood by a person of ordinary skill in the art. In some embodiments, the transition may be performed using the Equation 20 for mapping:

$$Y_{cor} = 1 + \frac{((P_y - Y_{min}) * (N_{col} - 1))}{Y_{max} - Y_{min}} \quad (20)$$
$$Z_{cor} = 1 + \frac{((P_Z - Z_{min}) * (N_{row} - 1))}{Z_{max} - Z_{min}}$$

where $N_{col}$ and $N_{row}$ are the column and row numbers, respectively; $P_y$ and $P_z$ are the pixel locations in the column and row locations, respectively; $Y_{min}$ is the least-valued point of the y axis from the sensor data of the ocular surface; $Y_{max}$ is the most-valued point; $Z_{min}$ is the least-valued point of the z axis from the sensor data point of the ocular surface; $Z_{max}$ is the most-value point of the z axis from the sensor data point of the ocular surface; and $Y_{cor}$ and $Z_{cor}$ are the sensor locations in the eye model corresponding to the $P_y$ and $P_z$ pixels of the ocular surface thermal image 260.

Zero or missing values may be validated. Once the temperature values are mapped from the 2D of the thermal image to 3D sensor data points of the ocular surface of the eye model 400, the eye model 400 may be electronically stored as an observed input value that may be used to estimate the temperature at the back of the eye using inverse analysis and optimization. In some embodiments, models of heat transfer may be used to map between core temperature and temperatures on the ocular surface.

In step 380, the temperature at the back of the eye is estimated using the eye model 400. The estimate may be obtained using a gradient-based or non-gradient-based optimization procedure to estimate the core body temperature at the back of the eye that produces the ocular surface temperature profile that best fits the data according to some merit function. For the temperature estimation in step 380, the temperature data may be evaluated using a combination of forward and backward methods, otherwise known as inverse analysis. In one embodiment, the mathematical formulations of the eye model which may include a governing equation, formulated in Equation. 19, along with the goodness of fit test and non-gradient optimization are used to evaluate the surface temperature at the back of the eye. The inverse problem may be set up as a minimization function of temperature (T), where the analysis can be performed by iterative minimization of an object function. As an initial starting point, guess the value of T at the surface boundary of $\Gamma_1$ and solve the ocular surface temperature T at the surface boundary of $\Gamma_2$ and $\Gamma_3$ using a forward method. The estimated temperature data of the ocular surface (i.e. T at $\Gamma_2$ and $\Gamma_3$) may then undergo the goodness of fit test with the ocular surface temperature data obtained from the infrared camera where the convergence to the minimum of the objective function is assessed. Depending on the result of the fit, the initial guess may then be updated, and a new estimate of ocular surface temperature is evaluated. The iterative process continue until the objective function is satisfied, i.e. best core body temperature value is attained. To handle the iterative process, non-gradient-based optimization may be performed using Brent's method, golden section search method, downhill simplex, or a pattern search method; alternatively, a gradient-based technique such as steepest descent, conjugate gradient, the Broyden-Fletcher-Powell-Reeves method, or Newton's method may be used. The chi-square test may be used to assess the goodness of fit test between the estimated and infrared measured ocular surface temperature data.

Equation 21 shows formulation of the reduced chi-square ($\chi_{red}^2$) equation, in which $\chi_{red}^2$ is given by:

$$\chi_{red}^2 = \frac{1}{N} \sum_{i=1}^{N} \left( \frac{T_{IR}(r_i; \alpha) - T_i}{\varrho(T)} \right)^2 \quad (21)$$

where $T_{IR}$ represents the ocular surface temperature acquired from the thermal image; $T_i$ (where i=1 and 3) represents the estimated ocular surface temperature evaluated using Equation 19; r is the position of the temperature sensors, $\alpha$ is the optimization parameter described as a function of the core body temperature; and N is the total number of sensors located on the ocular surface area of the eye model. Herein $T_{IR}(r; \alpha)$ is fitted to N number of numerically generated ocular surface temperature data $(T_i)$. Since $\chi_{red}^2$ is formulated to account the noise inherited from the instrumentation error, $\varrho(T)$ is added to account for the noise equivalence difference temperature of the camera provided by the manufacturer. It should be noted that, since $\varrho(T)$ is uniform across the image, the method produces a core body temperature estimate that is independent of the accuracy rating of the camera.

For a single model assessment, the accuracy of the fitness is established based on the following criteria:

$\lambda_{red}^2 > 1$—Poor fit.
$\lambda_{red}^2 \approx 1$—Good fit.
$\lambda_{red}^2 < 1$—Over fit.

In step 390, the estimated core body temperature and (optionally) the model 400 may be transmitted to the output device 140.

Figure 4A:
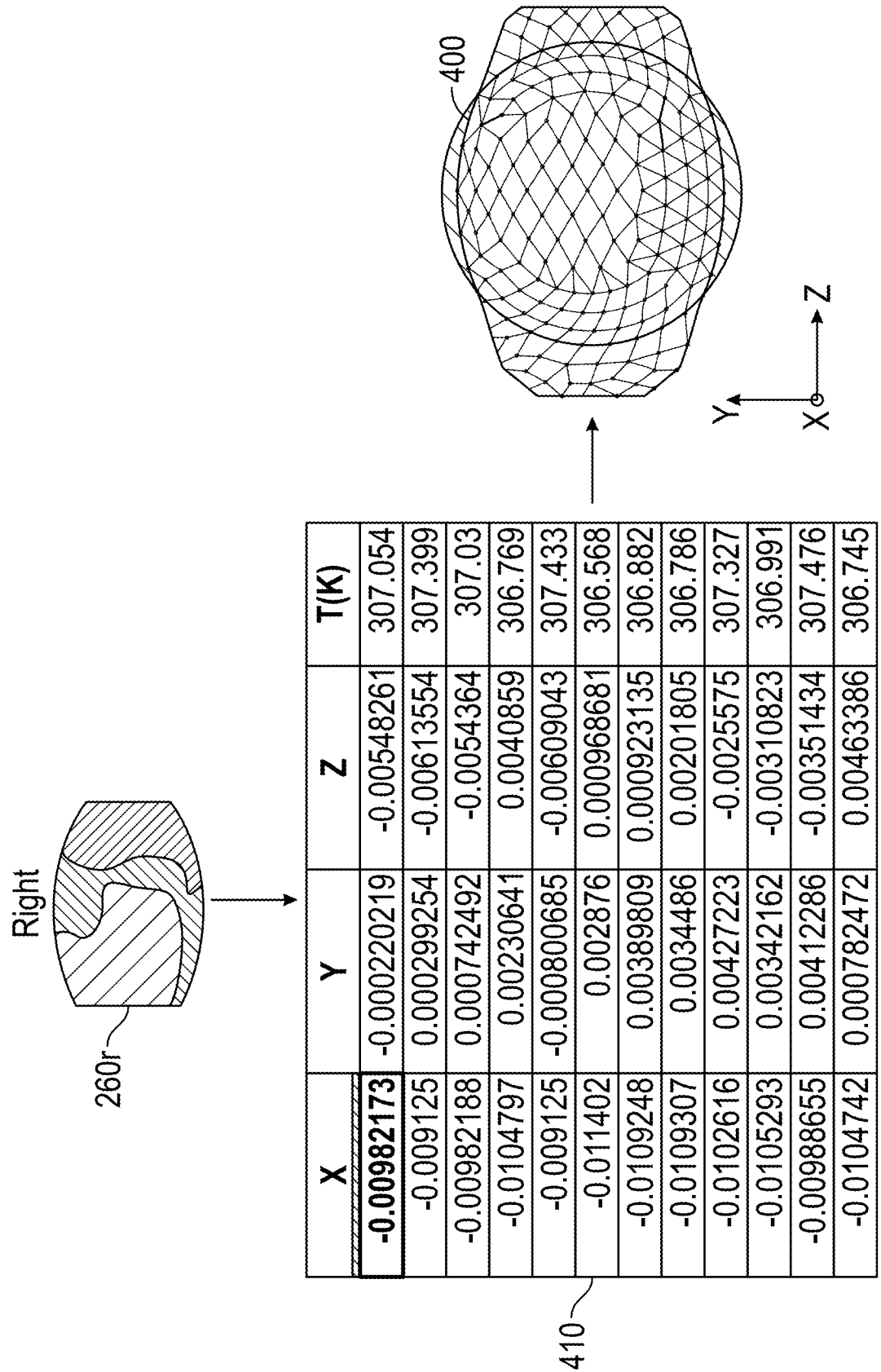
FIG. 4A is a diagram of the temperature data of the eye being applied to a model of an ocular surface of the eye according to one embodiment of the present disclosure.
Figure 4B:
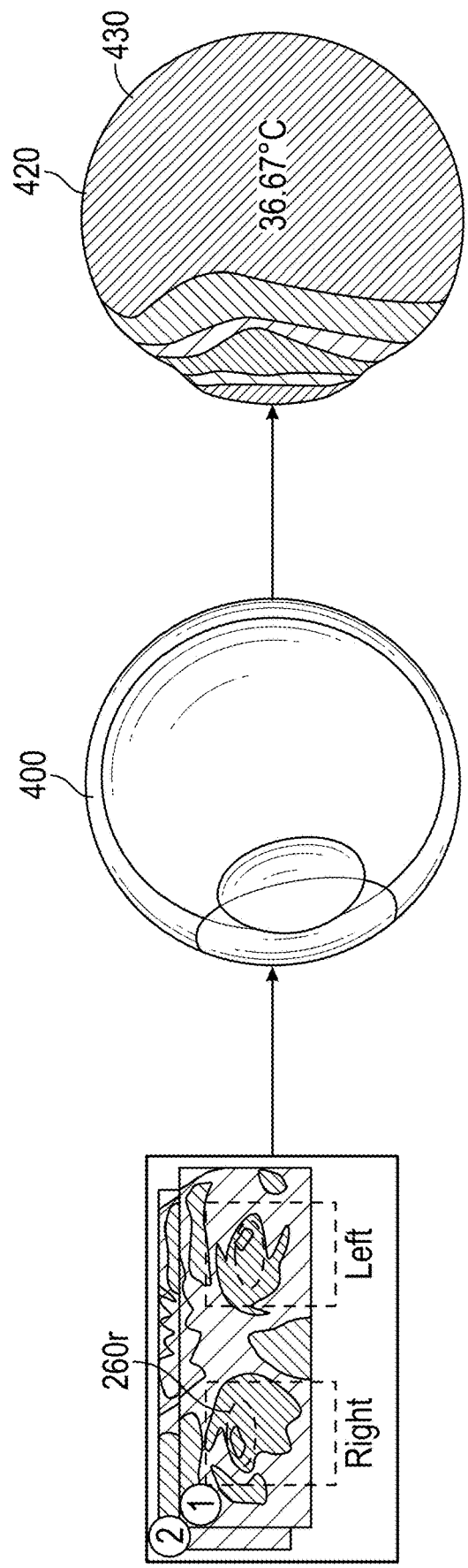
FIG. 4B is a diagram of the application of the temperature data being applied to the model of the eye surface according to one embodiment of the present disclosure.

FIGS. 4A-4B show diagrams of temperature data being applied a model of the eye. In FIG. 4A, the thermal image of the right eye 260*r* is converted into coordinates 410 which relate to the finite element mesh 400. In FIG. 4B, the thermal image of the right eye 260*r* is shown being mapped to the mesh 400 which is used to form the eye model 420 with a back of the eye 430.

While embodiments in the present disclosure have been described in some detail, according to the preferred embodiments illustrated above, it is not meant to be limiting to modifications such as would be obvious to those skilled in the art.

The foregoing disclosure and description of the disclosure are illustrative and explanatory thereof, and various changes in the details of the illustrated apparatus and system, and the construction and the method of operation may be made without departing from the spirit of the disclosure.

What is claimed is:

1. A system for measuring a body temperature of a subject based on thermal data collected by an infrared camera, the system comprising:
   a processing unit comprising one or more processors;
   one or more memories storing at least one three-dimensional model representing a geometry of an eye and instructions configured to be executed by the processing unit, the three-dimensional model comprising a model ocular surface and a model back portion opposite the model ocular surface, wherein the system is configured to:
   receive the thermal data collected by the infrared camera, the thermal data comprising a plurality of thermal measurements having respective pixel positions;
   determine an ocular surface portion of the thermal data that corresponds to a subject ocular surface of the subject;
   transition, based on the pixel positions, the thermal measurements of the ocular surface portion of the thermal data to locations on the model ocular surface on the three-dimensional model representing the geometry of the eye that correspond to locations on the subject ocular surface from which the thermal measurements were collected; and
   based on the thermal data, as transitioned to the model ocular surface of the three-dimensional model, determine a temperature at the model back portion of the three-dimensional model, wherein the determined temperature at the model back portion indicates the body temperature of the subject; and
   transmit the determined temperature to an output device.

2. The system of claim 1, wherein determining the temperature at the model back portion of the three-dimensional model comprises calculating what the temperature at the model back portion of the three-dimensional model must be to produce the observed thermal data, as transitioned to the model ocular surface, based on known boundary conditions and environmental conditions.

3. The system of claim 2, wherein the environmental conditions include a convective heat transfer parameter of air adjacent to the subject.

4. The system of claim 1, wherein the system is further configured to obtain the thermal data using the infrared camera.

5. The system of claim 1, wherein determining an ocular surface portion of the thermal data is performed using an optical image of the subject that indicates a location of the subject ocular surface of the subject.

6. The system of claim 5, wherein the system is further configured to process the thermal data and/or the optical image to correct for differences in one or more of: (i) image sizes, (ii) orientations, or (iii) fields of view.

7. The system of claim 5, wherein the system is further configured to obtain the thermal data using the infrared camera and to obtain the optical image using an optical camera.

8. The system of claim 1, wherein the determined temperature indicates a core body temperature of the subject.

9. The system of claim 1, wherein the three-dimensional model representing the geometry of the eye comprises representations of a cornea, an anterior humor, a vitreous humor, a lens, a retina, a choroid, an iris, a ciliary body, and a sclera.

10. The system of claim 1, wherein the output device comprises a display.

11. A method for measuring a body temperature of a subject based on thermal data collected by an infrared camera, the method being performed using a processing unit comprising one or more processors and one or more memories storing at least one three-dimensional model representing a geometry of an eye and instructions configured to be executed by the processing unit, the three-dimensional model comprising a model ocular surface and a model back portion opposite the model ocular surface, the method comprising:
- receiving the thermal data collected by the infrared camera, the thermal data comprising a plurality of thermal measurements having respective pixel positions;
- determining an ocular surface portion of the thermal data that corresponds to a subject ocular surface of the subject;
- transitioning, based on the pixel positions, the thermal measurements of the ocular surface portion of the thermal data to locations on the model ocular surface on the three-dimensional model representing the geometry of the eye that correspond to locations on the subject ocular surface from which the thermal measurements were collected; and
- based on the thermal data, as transitioned to the model ocular surface of the three-dimensional model, determining a temperature at the model back portion of the three-dimensional model, wherein the determined temperature at the model back portion indicates the body temperature of the subject; and
- transmitting the determined temperature to an output device.

12. The method of claim 11, wherein determining the temperature at the model back portion of the three-dimensional model comprises calculating what the temperature at the model back portion of the three-dimensional model must be to produce the observed thermal data, as transitioned to the model ocular surface, based on known boundary conditions and environmental conditions.

13. The method of claim 12, wherein the environmental conditions include a convective heat transfer parameter of air adjacent to the subject.

14. The method of claim 11, wherein the method further comprises obtaining the thermal data using the infrared camera.

15. The method of claim 11, wherein determining an ocular surface portion of the thermal data is performed using an optical image of the subject that indicates a location of the subject ocular surface of the subject.

16. The method of claim 15, wherein the method further comprises processing the thermal data and/or the optical image to correct for differences in one or more of: (i) image sizes, (ii) orientations, or (iii) fields of view.

17. The method of claim 15, wherein the method further comprises obtaining the thermal data using the infrared camera and obtaining the optical image using an optical camera.

18. The method of claim 11, wherein the determined temperature indicates a core body temperature of the subject.

19. The method of claim 11, wherein the three-dimensional model representing the geometry of the eye comprises representations of a cornea, an anterior humor, a vitreous humor, a lens, a retina, a choroid, an iris, a ciliary body, and a sclera.

20. The method of claim 11, wherein the output device comprises a display.

* * * * *